(12) United States Patent
Crivello

(10) Patent No.: US 6,391,999 B1
(45) Date of Patent: May 21, 2002

(54) EPOXY ALKOXY SILOXANE OLIGOMERS

(75) Inventor: James Vincent Crivello, Clifton Park, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 09/489,405

(22) Filed: Jan. 21, 2000

Related U.S. Application Data

(63) Continuation-in-part of application No. 09/019,632, filed on Feb. 6, 1998, now Pat. No. 6,069,259.

(51) Int. Cl.[7] .............................................. C08G 77/08
(52) U.S. Cl. ...................... 528/12; 528/421; 528/418; 528/32; 528/33; 528/41; 556/458; 549/215; 525/477; 526/279
(58) Field of Search .................... 528/12, 421, 418, 528/32, 33, 41; 526/279

(56) References Cited

U.S. PATENT DOCUMENTS

| 5,019,607 A | | 5/1991 | Coltrain et al. ............. 523/435 |
| 5,035,894 A | * | 7/1991 | Lee et al. |
| 5,316,695 A | | 5/1994 | Wilkes et al. ............ 252/315.6 |
| 5,650,474 A | * | 7/1997 | Yamaya et al. |
| 6,011,079 A | * | 1/2000 | Dougherty et al. |

FOREIGN PATENT DOCUMENTS

EP   94113136   8/1994   ......... C09D/183/04

OTHER PUBLICATIONS

Encyclopedia of Polymer Science and Engineering, vol. 1, Edited by Mark et al., John Wiley & Sons, pp. 274–275, 1985.*

Crivello, J., & Mao, Z., "Synthesis of Novel Multifunctional Siloxane Oligomers using Sol–Gel Techniques and Their Photoinitiated Cationic Polymerization," Chem. Mater., vol. 9, pp. 1554–1561, 1997.

Crivello, J., & Mao, Z., "Preparation and Cationic Photopolymerization of Organic–Inorganic Hybrid Matrixes," Chem. Mater., vol. 9, pp. 1562–1569, 1997.

Crivello, J., Yang, B. Whan–Gi, K., "Synthesis and Electron–Beam Polymerization of 1–Propenyl Ether Functional Siloxanes, " Pure Appl. Chem., vol. A33(4), pp. 399–415, 1996.

Crivello, J., & Löhden, G., "Synthesis and Photopolymerization of 1–Propenyl Ether Functional Siloxanes," Chem. Mater., vol. 8, pp. 209–218, 1996.

* cited by examiner

Primary Examiner—Robert Dawson
Assistant Examiner—Kuo-Liang Peng
(74) Attorney, Agent, or Firm—Heslin Rothenberg Farley & Mesiti P.C.

(57) ABSTRACT

Polymerizable siloxane oligomers comprising a plurality of repeating units of formula A and at least one unit of formula B:

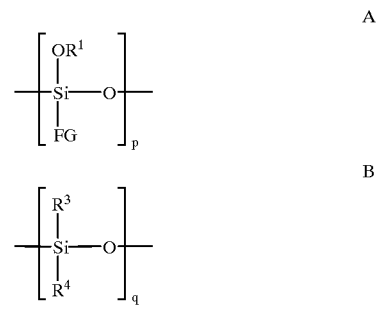

and terminating in a residue $R^2$ or $R^8$ are disclosed. In these formulae FG is a functional group, such as 2-(3,4-epoxycyclohexyl), and the R groups are alkyl, aryl, haloalkyl, aralkyl, alkoxy or aryloxy of 1 to 10 carbons. Processes for preparing the oligmers by hydrolysis/condensation of monomers of formula $(RO)_3Si\ FG$ and one or more alkoxy silane monomers of formula $R^3R^4R^8SiOR^{2a}$ are also disclosed, as are polymers resulting from the cationic polymerization of the oligomers.

23 Claims, No Drawings

EPOXY ALKOXY SILOXANE OLIGOMERS

CROSS REFERENCE TO RELATED APPLICATIONS

This application is a continuation-in-part of U.S. patent application Ser. No. 09/019,632, now U.S. Pat. No. 6,069,259, filed Feb. 6, 1998, the entire disclosure of which is incorporated herein by reference.

FIELD OF THE INVENTION

The invention relates to epoxy alkoxy siloxane oligomers.

BACKGROUND OF THE INVENTION

In recent years, there has been considerable interest in the photo, e-beam and thermally-induced cationic polymerization of siloxane-containing monomers and oligomers. Such monomers and oligomers have considerable potential in a wide diversity of applications including: non-stick release coatings, adhesives, abrasion resistant coatings for plastics, fiber optic coatings, reinforced composites and optical waveguides. The photopolymerizations of various multifunctional monomers characteristically proceeds only to low conversions due to trapping of residual reactive functional groups within the rigid, crosslinked network as it is formed. In this regard, siloxane containing monomers exhibit anomalous behavior that has been attributed to the conformational flexibility of the siloxane (Si—O—Si) bond and to free volume effects.

Preparation of multifunctional alkoxy siloxanes is difficult to accomplish by prior art methods. While epoxy-functional trialkoxy silanes are commercially available as starting materials, condensation polymerization of multifunctional alkoxy silanes generally results in crosslinked gels. Typically, alkoxy silanes such as tetraethoxysilane (TEOS) are subjected to acid or base catalyzed hydrolysis-condensation in the presence of controlled amounts of water to yield a gel. In most acid catalyzed sol-gel processes, HCl is used, while NaOH and $NH_4OH$ are often employed as base catalysts. However, it is difficult to reproducibly make intermediate, soluble, low viscosity, fluid oligomers. When such materials are obtained, they exhibit poor pot-lives and they gel on standing, due to further condensation.

In addition, the basic hydrolysis catalysts used in the sol-gel reaction are strong inhibitors for cationic polymerizations, and the traces of basic catalysts that remain in the product inhibit subsequent cationic polymerizations. On the other hand, acid hydrolysis catalysts are not generally useful for the synthesis of epoxy-functional siloxanes, since epoxy groups undergo spontaneous ring-opening reactions with acids.

There is therefore a need for a process for making pure multifunctional alkoxy siloxane oligomers reproducibly and in good yield. There is also a need for alkoxy siloxane oligomers that have long pot-lives and low viscosity and that cure rapidly and completely. There is also a need for oligomers that can be polymerized to polymers having such desirable properties as: exhibiting no glass transition at temperatures below 300° C.; having a relatively low coefficient of thermal expansion (CTE) between 0–180° C.; having a high storage modulus; and remaining stable at elevated temperatures.

SUMMARY OF THE INVENTION

In one aspect, the invention relates to a polymerizable siloxane oligomer comprising a plurality of repeating units of formula A and at least one unit of formula B:

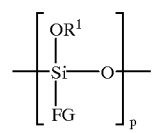

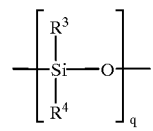

and terminating in a residue $R^2$ or $R^8$. In these formulae FG is a functional group. Each FG may be chosen from linear, branched and cyclic alkyl residues of 1 of 20 carbons terminating in a 1-alkenyl ether;

linear, branched and cyclic alkyl ether residues of 1 to 20 carbons and 1 to 9 oxygens terminating in a 1-alkenyl ether;

linear, branched and cyclic alkyl residues of 1 to 20 carbons terminating in an acrylate, an alpha-chloroacrylate, an alpha-cyanoacrylate or a methacrylate;

linear, branched and cyclic alkyl ether residues of 1 to 20 carbons and 1 to 9 oxygens terminating in an acrylate, an alpha-chloroacrylate, an alpha-cyanoacrylate or a methacrylate;

linear, branched and cyclic alkyl residues of 1 to 20 carbons substituted with an epoxide;

linear, branched and cyclic alkyl ether residues of 1 to 20 carbons and 1 to 9 oxygens substituted with an epoxide;

arylalkyl residues of 1 to 20 carbons substituted with an epoxide;

arylalkyl ether residues of 1 to 20 carbons and 1 to 9 oxygens substituted with an epoxide; and epoxy-functional organosiloxane residues of 1 to 20 silicons and 1 to 20 carbons.

R is alkyl, aryl, haloalkyl or aralkyl of 1 to 10 carbons;
$R^1$ is R,

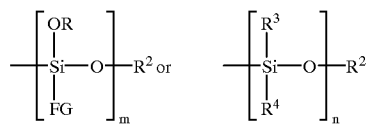

$R^2$ is alkyl, aryl, haloalkyl or aralkyl of 1 to 10 carbons or

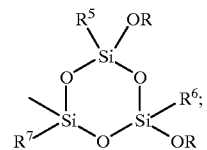

$R^3$ and $R^4$ are independently alkyl, aryl, haloalkyl, aralkyl, alkoxy or aryloxy of 1 to 10 carbons;
$R^5$, $R^6$ and $R^7$ are independently FG, alkyl, aryl, haloalkyl, aralkyl, alkoxy or aryloxy of 1 to 10 carbons;
$R^8$ is alkyl, aryl, haloalkyl, aralkyl, alkoxy or aryloxy of 1 to 10 carbons; m and n are independently 2 to 50; p is 2 to 50 and q is 1 to 50. Note that in this document, variables are defined when introduced and retain that definition throughout.

The foregoing oligomers may also be described in product-by-process terms as polymerizable siloxane oligomers produced by reacting one or more alkoxy silane monomers of formula $(RO)_3SiFG$ and one or more alkoxy silane monomers of formula $R^3R^4R^8SiOR^{2a}$ with 0.5 to 2.5 equivalents of water, in the presence of an ion exchange resin, optionally in the presence of a solvent, and separating the resin from the siloxane oligomer. In these monomers, $R^{2a}$ is alkyl, aryl, haloalkyl or aralkyl of 1 to 10 carbons.

In another aspect the invention relates to (1) polymers produced by cationically polymerizing one or more of the foregoing oligomers; and (2) polymers produced by cationically co-polymerizing one or more of the foregoing oligomers with an oligomer of formula:

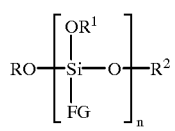

I

In another aspect the invention relates to a process for preparing a polymerizable siloxane oligomer comprising reacting one or more alkoxy silane monomers of formula $(RO)_3SiFG$ and one or more alkoxy silane monomers of formula $R^3R^4R^8SiOR^{2a}$ with 0.5 to 2.5 equivalents of water, in the presence of an ion exchange resin, optionally in the presence of a solvent, and separating the resin from the siloxane oligomer. The ion exchange resin is preferably a quaternary ammonium resin.

DETAILED DESCRIPTION OF THE INVENTION

The polymerizable siloxane oligomers of the invention are made up of a plurality of repeating units of formula A and at least one unit of formula B:

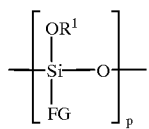

A

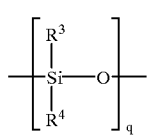

B

The oligomers of the invention may be block oligomers or random oligomers. Preferably the ratio of A to B (or p to q) is from 19:1 to 1:9, most preferably the ratio of A to B is from 1:1 to 3:1. In a preferred embodiment, FG is one or more residues chosen from formulae A–Q:

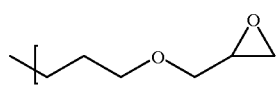

A

-continued

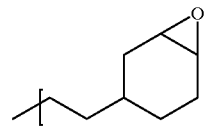

B

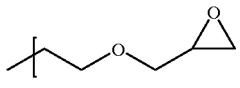

C

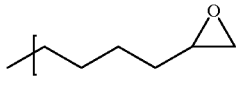

D

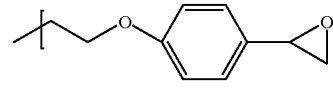

E

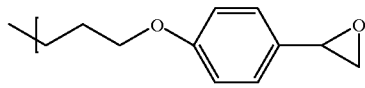

F

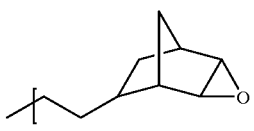

G

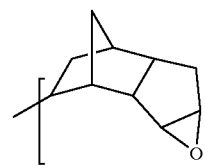

H

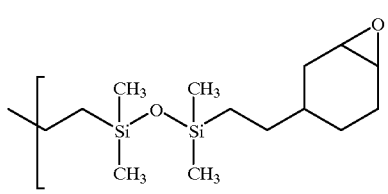

J

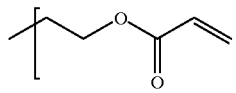

K

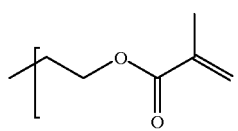

L

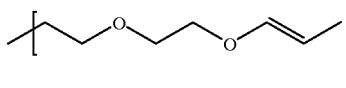

M

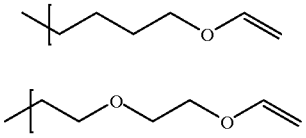

N

O

-continued

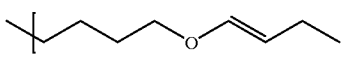

P

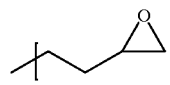

Q

From among these residues, 2-(3,4-epoxycyclohexylethyl), 3-glycidoxypropyl and 1-propenoxy-2-ethoxyethyl are preferred. In an another preferred embodiment, $R^1$ is methyl or ethyl; $R^2$ is methyl, methoxy, ethyl, ethoxy, phenyl or

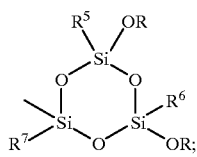

$R^3$, $R^4$ and $R^8$ are chosen independently from methyl, methoxy, ethyl, ethoxy, and phenyl; and $R^5$, $R^6$ and $R^7$ are chosen independently from methyl, methoxy, ethyl, ethoxy, phenyl and FG.

As will be apparent to the artisan, the ratios of residues represented by $R^5$, $R^6$ and $R^7$ in a random oligomer will reflect the ratio and relative reactivities of A to B in the monomer mix from which the oligomer was prepared.

The siloxanes of the invention are straight- or branched-chain oligomers and may additionally contain one or more cyclic structures composed of three monomer units as end groups, as depicted in the formula:

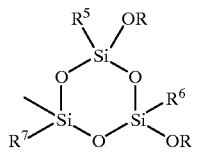

The presence of the ring structure is dependent on the number of equivalents of water employed in the reaction and on reaction conditions, including temperature and time. The oligomer chains are composed of from two to fifty siloxane monomer units, preferably of from two to twenty monomer units.

The effective molecular weight and viscosities of the oligomers of the invention may be varied according to the desired use, both of the oligomer and of the product polymer. For many purposes oligomers in which the sum of p and q is from 4 to 20 are preferred. The rate and extent of the hydrolysis-condensation reaction are dependent on the strength of the catalyst used. Strong acids or bases cause fast hydrolysis and condensation of alkoxysilanes and high conversions to oligomers. The reaction is well controlled with ion exchange resins as catalysts. Condensation in the presence of these catalysts proceeds at a convenient rate so that the reaction times are not inordinately long and at the same time slow enough that adequate control can be maintained over the reaction to provide reproducible molecular weight control and to avoid gelation.

The polymerizable siloxanes of the invention are synthesized by base-catalyzed hydrolysis and subsequent condensation of an alkoxy silane monomer of Formula $(RO)_3SiFG$ and one or more alkoxy silane monomers of formula $R^3R^4R^8SiOR^{2a}$. In the above formula, it is preferred that the alkoxy group (RO) is methoxy or ethoxy and that the functional group FG not be polymerizable at a rate comparable to that of the alkoxy siloxane. As defined above, $R^{2a}$ is alkyl, aryl, haloalkyl or aralkyl of 1 to 10 carbons and $R^3$, $R^4$ and $R^8$ are independently alkyl, aryl, haloalkyl, aralkyl, alkoxy or aryloxy of 1 to 10 carbons. Preferably, $R^{2a}$ is methyl or ethyl and $R^3$, $R^4$ and $R^8$ are chosen independently from methyl, methoxy, ethyl, ethoxy, and phenyl. Monomers that provide the "B" units include: tetraethoxysilane (ethylorthosilicate), tetramethoxysilane (methylorthosilicate), tetraisopropoxysilane, methyltrimethoxysilane, ethyltriethoxysilane, hexyltriethoxysilane, cyclohexyltrimethoxysilane, 1,1,1-trifluoroethyltriethoxysilane, phenyltriethoxysilane, phenylmethyldiethoxysilane, phenylmethyldimethoxysilane, diphenyldimethoxysilane, 2-phenylethyltrimethoxysilane, benzyltriethoxysilane, vinyltrimethoxysilane, dimethyldimethoxysilane, trimethylmethoxysilane, diethyldimethoxysilane, allyltrimethoxysilane, divinyldimethoxysilane, methyvinyldimethoxysilane, bis(triethoxysilyl)methane, bis (triethoxysilyl)ethane, butenyltrimethoxysilane, 3-bromopropyltrimethoxysilane, 2-chloroethylmethyldimethoxysilane, 1,1,2,2-tetramethoxy-1,3-dimethyldisiloxane, phenyltrimethoxysilane. Also, useful in these mixtures are trimethoxysilyl-terminated polydimethylsiloxanes as well as the corresponding hydroxyl-terminated polydimethylsiloxanes. The foregoing monomers are either commercially available or readily synthesized by reactions well known in the art.

The ion exchange resin catalyzed sol-gel copolycondensation can be conducted simultaneously with all the components to provide a random distribution of the resulting repeating units derived from A and B in the oligomer. Alternatively, the reaction can be conducted in a sequential fashion. In this latter case, a second alkoxysilane of either structure A or B is added after the first substrate has been consumed by reaction. This results in an oligomer in which like repeating units occur together in a block structure.

The reaction is typically carried out in a solvent in which both the starting silane monomer and the siloxane product are soluble. Alcohols such as ethanol, t-butanol, n-propanol and isopropanol are preferred.

The reaction may be conducted at temperatures sufficient to maximize the rate of reaction while minimizing undesirable side reactions, generally from 0–100° C. and preferably from 35–70° C. At higher temperatures, the reaction is completed in a shorter time. For example, a reaction conducted at 45° C. may be complete at 24 hours, while a similar reaction carried out at 60° C. is complete in 12 hours. The extent of reaction may be determined by $^1H$ NMR spectroscopy, by monitoring the consumption of alkoxy groups The degree of condensation may be controlled by varying the ratio of water to silane in the reaction mixture. Higher ratios of water result in an increase in the rate of the hydrolysis-condensation reaction and also in a greater proportion of oligomers with higher molecular weights. For example, reactions at 60° C. with 1.0 and 1.5 equivalents of water will result in a broad distribution of oligomeric products in both cases, with a greater proportion of higher molecular weight material in reactions with 1.5 equivalents than in reactions with 1.0 equivalents of water. For some uses, the viscosity of the oligomer may be from 100 to 1,000,000 cps; for other uses, oligomers having a viscosity of 500 cps to 5000 cps are preferred; for yet other uses, the reaction is carried to high molecular weight, and the oligomer which is isolated is a very high viscosity liquid or a glassy solid. One set of preferred oligomers according to the process has an apparent molecular weight of 3000 to 10,000.

Various basic ion exchange resins may be employed as catalysts in the processes of this invention. For example, strongly basic ion exchange resins such as Amberlite A-27, Amberlite IRA-400 and Amberlite IRA-904 from Rohm and Haas Corp. having the structure depicted below have been employed.

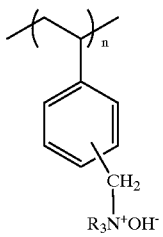

Most advantageously, the ion exchange resin is in a crosslinked bead form that permits recovery from the reaction mixture by simple filtration. The ion-exchange resin catalyst may be reused in subsequent sol-gel reactions. Alternatively, the condensations may be carried out in a continuous fashion on a fixed bed of the resin. The hydrolysis/condensation reaction does not appear limited by porosity or ion-exchange capacity of the resin. Exemplary styrene-divinyl benzene resins useful in the practice of the invention are Amberlyst® and Amberlite®, Rohm & Haas Company; Ionac®, Sybron Chemicals; Dowex®, Dow Chemical; NRW®, Purolite; Tulsion®, Thermax, Ltd; and the CG and SBG lines of resins from Resintech, Inc. Removal of the catalyst prevents further reaction of the oligomer leading to crosslinking, and results in a product which retains its initial viscosity during storage. The oligomers of the invention possess good shelf stability, showing no increase in viscosity on standing for more than two months.

After removal of the solvent, the resulting multifunctional siloxane oligomers may be further polymerized via the functional groups FG by various means. For example, the epoxy functional oligomers may be combined with amine or anhydride curing agents and polymerized by traditional thermal methods. Acrylate and methacrylate functional oligomers may be similarly thermally cured through the use of peroxide and azo free radical initiators. Alternatively, these oligomers may be also photopolymerized. Epoxy, 1-propenyl ether, 1-butenyl ether and vinyl ether functional oligomers can be photopolymerized using UV or visible irradiation in the presence of diaryliodonium, dialkylphenacylsulfonium, triarylsulfonium salt, and ferrocenium salt photoinitiators. The aforementioned oligomer-photoinitiator mixtures may be also effectively cured in the presence of the above onium salts using e-beam irradiation. By the use of the proper onium catalyst and/or the addition of copper compounds as co-catalysts, the oligomers may be thermally cured. Acrylate and methacrylate oligomers may be photopolymerized using a plethora of free radical photoinitiators including for example, benzoin, benzoin alkyl ethers, 1,1-diethoxyacetophenone, 1-benzoylcyclohexanol and many others.

The oligomers and the polymers resulting from the polymerization of the oligomers of the invention have many applications. For example, the polymers may be employed as protective and abrasion resistant coatings for wood, metals, plastics and glass. They may be employed as adhesive or bonding agents. Combined with fibrous reinforcing agents the oligomers may be cured by UV and e-beam radiation and/or heat to give high performance composites. They may be further used as curable encapsulating and potting agents for electronic and microelectronic applications. Further uses lie in resins for stereolithography, holographic recording media and as optical adhesives, fiber optic coatings, waveguides in photonic applications and for other applications requiring high mechanical strength, stability at high temperatures, and high rate of cure. In the course of their use in various applications, the oligomers may be combined with various fibrous or particulate reinforcing agents, flow control and flatting agents, photosensitizers, pigments and dyes and mold releases.

The cationic polymerization initiator is preferably a diazonium, sulfonium, phosphonium, or iodonium salt. A preferred initiator is a diaryliodonium salt selected from the group having formulae (II), (III), (IV), and (V)

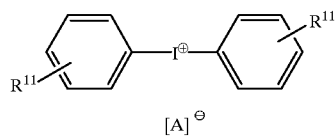

(II)

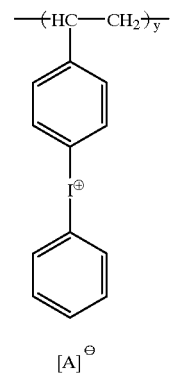

(III)

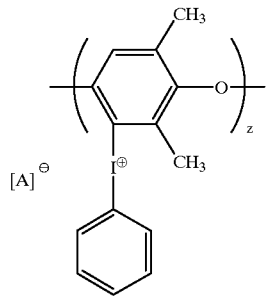

(IV)

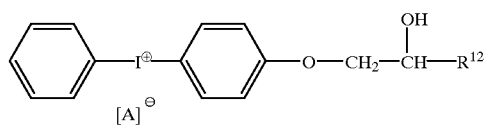

(V)

wherein each $R^{11}$ is independently hydrogen, $C_1$ to $C_{20}$ alkyl, $C_1$ to $C_{20}$ alkoxyl, $C_1$ to $C_{20}$ hydroxyalkoxyl, halogen, and nitro; $R^{12}$ is $C_1$ to $C_{30}$ alkyl or $C_1$ to $C_{30}$ cycloalkyl; y and z are each independently integers having a value of at least 5; $[A]^\ominus$ is a non-nucleophilic anion, commonly $SbF_6^\ominus$, $BF_4^\ominus$, $PF_6^\ominus$, $AsF_6^\ominus$, or $(C_6F_5)_4B^\ominus$.

Another preferred cationic polymerization initiator is a phenylacylsulfonium salt having formula (VI)

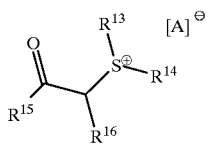

(VI)

wherein $R^{13}$ is a $C_1$ to $C_{30}$ monovalent organic radical; $R^{14}$ is a $C_1$ to $C_{30}$ monovalent organic radical, or $R^{13}$ and $R^{14}$ taken together may form a 5 or 6-membered ring; $R^{15}$ is $C_6$ to $C_{20}$ alkyl, aryl, $C_6$ to $C_{20}$ substituted alkyl or substituted aryl; $R^{16}$ is hydrogen or $C_1$ to $C_8$ alkyl; and $[A]^\ominus$ is a non-nucleophilic anion, such as previously listed. $R^{14}$ may also be a photosensitizing residue.

Thermal cure of the epoxy resin can be effected through the use of the cationic polymerization initiator with or without the addition of a copper co-catalyst (accelerator). Furthermore, by changing the structures of the materials included with the oligomer and by varying their concentrations, the onset curing temperature and the speed of cure can be adjusted within a wide latitude. Curing can alternatively be induced by irradiation of the cationic polymerization initiator/epoxy resin by UV light (or at longer wavelengths as discussed below) or by e-beam. E-beam curing is described in U.S. Pat. Nos. 5,260,349 and 4,654,379. Curing agents are described in U.S. Pat. Nos. 4,842,800, 5,015,675, 5,095,053, and 5,073,643. Preferred diaryliodonium salts are [4-(2-hydroxy-1-tetradecyloxy)-phenyl] phenyliodonium hexafluoroantimonate, wherein in structure (V), $[A]^\ominus$ is $SbF_6^\ominus$, and $R^{12}$ is $C_{12}H_{25}$ (available from Polyset Company, Mechanicville, N.Y., as PC-2506); and wherein in structure (V), $[A]^\ominus$ is $PF_6^\ominus$, and $R^1$ is $C_{12}H_{25}$ (available from Polyset Company as PC2508). Triarylsulfonium salts, such as the mixture of S,S-diphenyl-4-thiophenoxyphenylsulfonium hexafluoroantimonate and bis(diphenylsulfonio)4,4'-diphenylsulfide bishexafluoroantimonate are commercially available from Polyset Company as PC2505. Dialkylphenacylsulfonium salts having the general formula (VI) are disclosed in U.S. Pat. No. 6,031,014 filed Dec. 8, 1998. The disclosures of the foregoing patents and application are incorporated herein by reference.

Definitions:

"Alkyl" is intended to include linear, branched, or cyclic hydrocarbon structures and combinations thereof. "Lower alkyl" refers to alkyl groups having from 1 to 4 carbon atoms. Examples of lower alkyl groups include methyl, ethyl, propyl, isopropyl, butyl, s-and t-butyl and the like. Preferred alkyl groups are those of $C_{20}$ or below. "Cycloalkyl" is a subset of alkyl and includes cyclic hydrocarbon groups of from 3 to 8 carbon atoms. Examples of cycloalkyl groups include c-propyl, c-butyl, c-pentyl, c-hexyl, norbornyl and the like.

"Alkoxy" or "alkoxyl" refers to groups of from 1 to 20 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower-alkoxy" refers to groups containing one to four carbons.

"Acyl" refers to groups of from 1 to 20 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl, t-butoxycarbonyl, benzyloxycarbonyl and the like. "Loweracyl" refers to groups containing one to four carbons.

"Aryl" refers to a 5- or 6-membered aromatic ring; a bicyclic 9- or 10-membered, partially or fully aromatic ring system; or a tricyclic 13- or 14-membered partially or fully aromatic ring system optionally substituted with 1–3 lower alkyl, halo lower alkyl, =O, —$NO_2$, halogen, hydroxy, alkoxy, cyano, phenyl, benzyl, phenoxy or benzyloxy. The aromatic 6- to 14-membered carbocyclic rings include, e.g., benzene, naphthalene, indane, tetralin, and fluorene.

"Arylalkyl" means an alkyl residue attached to an aryl ring. Examples are benzyl, phenethyl and the like.

The following examples are included by way of exemplification and are not intended to imply any limitation.

EXAMPLES 1 and 2

Sol-gel condensations of 2-(3,4-epoxycyclohexyl) ethyl trimethoxysilane

Preparations of O1 and O2

A 50 mL round bottom flask fitted with a magnetic stirrer, reflux condenser and a thermometer was charged with 246.4 g (1 mol) of 2-(3,4-epoxycyclohexyl)ethyl-trimethoxysilane, 1.5 equivalents (27 g) of deionized water, 8 g of Amberlite IRA-400 ion exchange resin, and 50 mL of isopropanol. The colorless solution was stirred and heated at reflux (~80° C.) for 4 hours (O2) and 6 hours (O1). After the designated reaction time, the solvent was removed under reduced pressure and the resulting in a colorless, viscous liquid. Oligomers were further characterized by $^1H$ NMR spectroscopy and by RTIR analysis.

EXAMPLES 3–6

Sol-gel condensations of 2-(3,4-epoxycyclohexyl) ethyltrimethoxysilane with methyltrimethoxysilane, phenyltrimethoxysilane, methyl phenyldimethoxysilane and diphenyldimethoxysilane In a manner similar to examples I and 2, there were combined in a 500 mL round bottom flask fitted with a magnetic stirrer, reflux condenser and a thermometer, 0.7 equivalents (172.5 g) of 2-(3,4-epoxycyclohexyl) ethyltrimethoxy silane and 0.3 equivalents of methyltrimethoxysilane (to produce oligomer O3), phenyltrimethoxysilane (to produce oligomer O4), 0.3 equivalents of methyl phenyldimethoxysilane (to produce oligomer O5) or 0.3 equivalents of diphenyldimethoxysilane (to produce oligomer O6). To this mixture was added 1.5 equivalents (27 g) of deionized water, 8 g of Amberlite IRA-400 ion exchange resin, and 50 mL of isopropanol. The colorless solution was stirred and heated at reflux (~80° C.) for 22 hours for O3 and 12 hours for O4, O5 and O6. After the designated reaction time, the solvent was removed under reduced pressure and the resulting colorless, viscous liquid oligomers were obtained.

EXAMPLES 7–10

Thermal polymerization of oligomers O3–O6

To each of the above resins was added 2% by weight of a 50% solution of 4(2-hydroxy-1-tetradecyloxyphenyl) phenyliodonium hexafluoroantimonate dissolved in 3,4-epoxycyclohexylmethyl 3',4'-epoxycyclohexanecarboxylate (Union Carbide ERL-4221E). Four grams of the mixture was placed into a shallow aluminum pan and the pan placed in a forced air oven at 165° C. for 1.5 hours. Transparent, colorless cured resin castings were obtained. The cured samples were removed from the pan and then cut into bar specimens for mechanical and thermal testing. The results of those tests are given in Table 1.

In general, the modified resins (O3–O6) display comparable mechanical and thermal characteristics to the unmodified resins (O1 and O2) and, in addition, display better resistance to cracking and crazing. The very small changes of the CTE values throughout the temperature range from 0–200° C. are indicative of a very highly crosslinked system.

TABLE 1

Results of Mechanical and Thermal Testing of Resins

| Property | O3 | O2 | O4 | O5 | O6 | O1 |
|---|---|---|---|---|---|---|
| Curing characteristics | | | | | | |
| cracking | — | minor | no | no | no | minor |
| crazing | — | minor | minor | no | no | yes |
| separation | — | yes | yes | yes | yes | yes |
| DSC Cure* | | | | | | |
| ΔH(J/g) | 171 | 312 | 300 | 322 | 280 | 283 |
| onset(° C.) | 182 | 160 | 140 | 140 | 140 | 170 |
| Peak(° C.) | 191 | 168 | 160 | 163 | 167 | 182 |
| peak height(MW) | 38 | 34 | 24 | 18 | 15 | 49 |
| CTE# | | | | | | |
| 0–100(° C.) | 95 | 80 | 107 | 105 | 95 | 65 |
| 0–200(° C.) | 105 | 92 | 128 | 120 | 110 | 73 |
| 100–200(° C.) | 115 | 104 | 150 | 139 | 125 | 83 |
| Storage Modulus | | | | | | |
| 25° C. (GPa) | 0.850 | .850 | 1.16 | 0.925 | 0.820 | 1.6 |
| 150° C. (GPa) | 0.650 | 0.720 | 0.53 | 0520 | 0.480 | 1.3 |
| Δ(MPa)† | 200 | 130 | 630 | 405 | 340 | 300 |
| Viscosity | | | | | | |
| @25° C.(cps) | 78000 | 23000 | 11500 | 30200 | semisolid | semisolid |
| @65° C.(cps) | 3617 | 1320 | — | — | 15500 | 14000 |

*Heating rate 10° C./min in air.
Coefficient of thermal expansion.
†Change in modulus from 25–150 ° C.

EXAMPLES 11–16

Mixtures of Modified and Unmodified Resins

Combined and thermally cured were 50/50 wt % mixtures of O1 or O2 with modified resins O4–O6. The compositions are given in Table 2. The mechanical and thermal properties are depicted in Table 3.

TABLE 2

Compositions of Mixed Oligomers

| Example | 11 | 12 | 13 | 14 | 15 | 16 |
|---|---|---|---|---|---|---|
| O1 | 50 | 50 | 50 | — | — | — |
| O2 | — | — | — | 50 | 50 | 50 |
| O4 | 50 | — | — | 50 | — | — |
| O5 | — | 50 | — | — | 50 | — |
| O6 | — | — | 50 | — | — | 50 |

The thermal and mechanical properties of the thermally cured mixtures of O1 or O2 with the modified resins O4–O6 are excellent.

TABLE 3

Results of Mechanical and Thermal Testing of Resins Mixtures

| Property | 11 | 12 | 13 | 14 | 15 | 16 |
|---|---|---|---|---|---|---|
| Curing characteristics | | | | | | |
| Cracking | no | no | no | no | no | no |
| Separation | yes | yes | yes | yes | yes | yes |
| Crazing | minor | no | no | yes | no | no |
| DSC Cure* | | | | | | |
| ΔH(J/g) | 254 | 241 | 244 | 245 | 244 | 243 |
| onset(° C.) | 140 | 160 | 160 | 160 | 160 | 160 |
| Peak(° C.) | 173 | 179 | 180 | 174 | 177 | 177 |
| Peak hight | 39 | 41 | 39 | 56 | 37 | 39 |
| CTE# | | | | | | |
| 0–100(° C.) | 104 | 98 | 80 | 112 | 105 | 100 |
| 0–200(° C.) | 116 | 108 | 90 | 122 | 115 | 110 |
| 100–200(° C.) | 127 | 118 | 100 | 132 | 125 | 120 |
| Storage Modulus | | | | | | |
| 25° C.(GPa) | 1.2 | 1.3 | 1.4 | 1.2 | 1.25 | 1.2 |
| 150° C. (GPa) | 0.746 | 0.889 | 1.01 | 0.765 | 0.849 | 0.849 |
| Δ(MPa)† | 451 | 422 | 390 | 440 | 397 | 357 |

*Heating rate 10° C./min in air.
Coefficient of thermal expansion.
†Change in modulus from 25–150 ° C.

EXAMPLE 17

Amine Cure

To 10 g of a resin (04) prepared by the condensation of 3 parts of phenyltrimethoxysilane and 7 parts of 4(2-Trimethoxysilylethyl)epoxycyclohexane there were added 3.5 g Epi-cure 826 amine hardener from the Shell Company. The blend was thoroughly mixed, poured into a shallow pan and then allowed to stand at 50° for 1 hour in a forced air oven. At the end of this time, the reaction mixture was found to consist of a hard, insoluble, crosslinked resin.

EXAMPLE 18

Anhydride Cure

To 10 g of a resin (05) prepared by the condensation of 3 parts of diphenyldimethoxysilane and 7 parts of 4(2-Trimethoxysilylethyl)epoxycyclohexane there were added 3.5 g hexahydrophthalic anhydride. The blend was thoroughly mixed, poured into a shallow pan and then allowed to stand at 165° for 1 hour in a forced air oven. At the end of this time, the reaction mixture was found to consist of a hard, insoluble, crosslinked resin.

I claim:
1. A polymerizable siloxane oligomer produced by
   a. reacting one or more alkoxy silane monomers of formula $(RO)_3SiFG$ and one or more alkoxy silane monomers of formula $R^3R^4R^8SiOR^{2a}$ with 0.5 to 2.5 equivalents of water, in the presence of an ion exchange resin, optionally in the presence of a solvent; and
   b. separating the resin from said siloxane oligomer;
   wherein:
   FG has a structure independently chosen for each monomer from the group consisting of:
      linear, branched and cyclic alkyl residues of 1 to 20 carbons terminating in a 1-alkenyl ether;
      linear, branched and cyclic alkyl ether residues of 1 to 20 carbons and 1 to 9 oxygens terminating in a 1-alkenyl ether;
      linear, branched and cyclic alkyl residues of 1 to 20 carbons terminating in an acrylate, an alpha-chloroacrylate, an alpha-cyanoacrylate or a methacrylate;
      linear, branched and cyclic alkyl ether residues of 1 to 20 carbons and 1 to 9 oxygens terminating in an acrylate, an alpha-chloroacrylate, an alpha-cyanoacrylate or a methacrylate;
      linear, branched and cyclic alkyl residues of 1 to 20 carbons substituted with an epoxide;
      linear, branched and cyclic alkyl ether residues of 1 to 20 carbons and 1 to 9 oxygens substituted with an epoxide;
      arylalkyl residues of 1 to 20 carbons substituted with an epoxide;
      arylalkyl ether residues of 1 to 20 carbons and 1 to 9 oxygens substituted with an epoxide; and
      epoxy-functional organosiloxane residues of 1 to 20 silicons and 1 to 20 carbons;
   where
   R is alkyl, aryl, haloalkyl or aralkyl of 1 to 10 carbons;
   $R^{2a}$ is alkyl, aryl, haloalkyl or aralkyl of 1 to 10 carbons; and
   $R^3$, $R^4$ and $R^8$ are independently alkyl, aryl, haloalkyl, aralkyl, alkoxy or aryloxy of 1 to 10 carbons.

2. A polymerizable oligomer according to claim 1 having a molecular weight between 3000 and 10,000.

3. A polymerizable siloxane oligomer according to claim 1, wherein FG has a structure independently chosen for each monomer from the group consisting of the structures of Formulae A–Q:

A

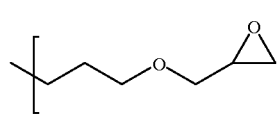

4. A polymerizable siloxane oligomer according to claim 1, wherein FG for each monomer is independently 2-(3,4-epoxycyclohexyl)ethyl or 3-glycidoxypropyl.

5. A polymerizable siloxane oligomer according to claim 1, wherein R is methyl or ethyl and $R^3$, $R^4$ and $R^8$ are chosen independently from methyl, methoxy, ethyl, ethoxy, and phenyl.

6. A process for preparing a polymerizable siloxane oligomer comprising:
   a. reacting one or more alkoxy silane monomers of formula $(RO)_3SiFG$ and one or more alkoxy silane monomers of formula $R^3R^4R^8SiOR^{2a}$, with 0.5 to 2.5 equivalents of water, in the presence of an ion exchange resin, optionally in the presence of a solvent; and
   b. separating the resin from said siloxane oligomer;
      wherein FG has a structure independently chosen for each monomer from the group consisting of:
         linear, branched and cyclic alkyl residues of 1 to 20 carbons terminating in a 1-alkenyl ether;
         linear, branched and cyclic alkyl ether residues of 1 to 20 carbons and 1 to 9 oxygens terminating in a 1-alkenyl ether;
         linear, branched and cyclic alkyl residues of 1 to 20 carbons terminating in an acrylate, an alpha-chloroacrylate, an alpha-cyanoacrylate or a methacrylate;
         linear, branched and cyclic alkyl ether residues of 1 to 20 carbons and 1 to 9 oxygens terminating in an acrylate, an alpha-chloroacrylate, an alpha-cyanoacrylate or a methacrylate;
         linear, branched and cyclic alkyl residues of 1 to 20 carbons substituted with an epoxide;
         linear, branched and cyclic alkyl ether residues of i to 20 carbons and 1 to 9 oxygens substituted with an epoxide;
         arylalkyl residues of 1 to 20 carbons substituted with an epoxide;
         arylalkyl ether residues of 1 to 20 carbons and 1 to 9 oxygens substituted with an epoxide; and
         epoxy-functional organosiloxane residues of 1 to 20 silicons and 1 to 20 carbons;
      where
      R is alkyl, aryl, haloalkyl or aralkyl of 1 to 10 carbons;
      $R^{2a}$ is alkyl, aryl, haloalkyl or aralkyl of 1 to 10 carbons; and $R^3$, $R^4$ and $R^8$ are independently alkyl, aryl, haloalkyl, aralkyl, alkoxy or aryloxy of 1 to 10 carbons.

7. A process according to claim, 6 wherein said ion exchange resin is a quaternary ammonium resin.

8. A process according to claim 6, wherein FG has a structure independently chosen for each monomer from the group consisting of the structures of Formulae A–Q:

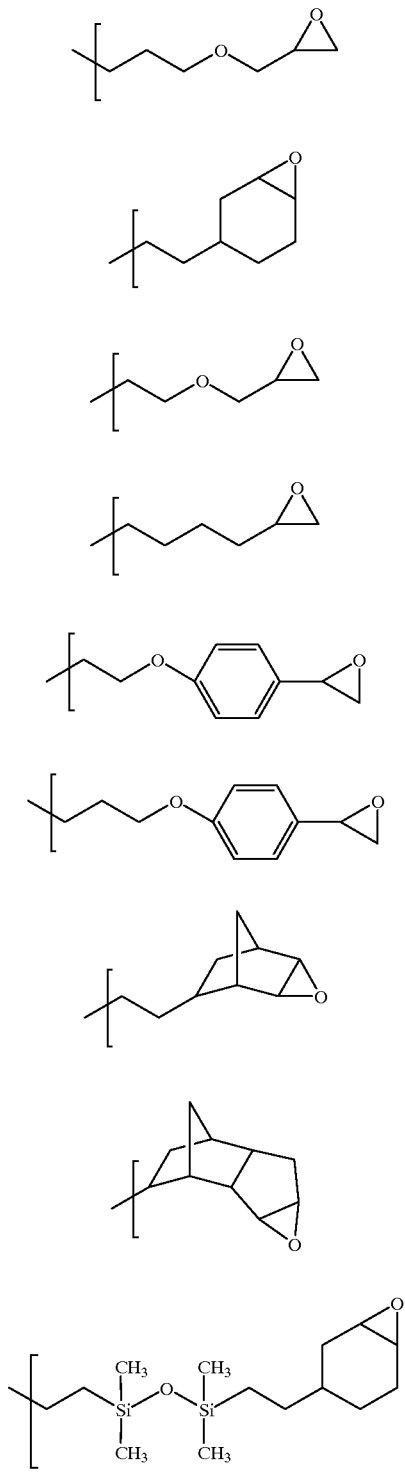

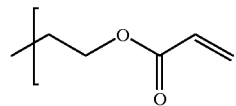

K

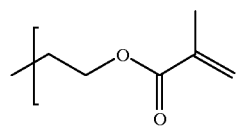

L

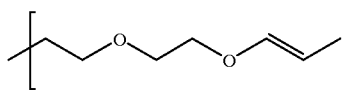

M

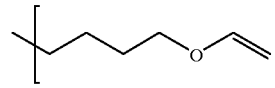

N

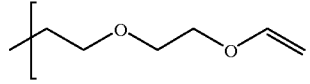

O

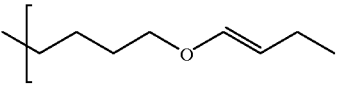

P

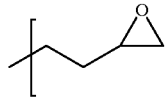

Q

9. A process according to claim 6, wherein R is methyl or ethyl and $R^3$, $R^4$ and $R^8$ are chosen independently from methyl, methoxy, ethyl, ethoxy, and phenyl.

10. A polymerizable oligomer according to claim 1, wherein the ratio of alkoxy silane monomers of formula $(RO)_3SiFG$ to the alkoxy silane monomers of formula $R^3R^4R^8SiOR^{2a}$ ranges from 19:1 to 1:9, by weight.

11. A polymerizable oligomer according to claim 1, wherein the ratio of alkoxy silane monomers of formula $(RO)_3SiFG$ to the alkoxy silane monomers of formula $R^3R^4R^8SiOR^{2a}$ ranges from 3:1 to 1:1, by weight.

12. A polymerizable oligomer according to claim 1, wherein said one or more alkoxy silane monomers of formula $(RO)_3SiFG$ and one or more alkoxy silane monomers of formula $R^3R^4R^8SiOR^{2a}$ are reacted sequentially, and whereby a block oligomer is produced.

13. A polymerizable oligomer according to claim 1, wherein FG is chosen from linear, branched and cyclic alkyl residues of 1 to 20 carbons terminating in a 1-alkenyl ether; and linear, branched and cyclic alkyl ether residues of 1 to 20 carbons and 1 to 9 oxygens terminating in a 1-alkenyl ether.

14. A polymerizable oligomer according to claim 1, wherein FG is chosen from linear, branched and cyclic alkyl residues of 1 to 20 carbons terminating in an acrylate, an alpha-chloroacrylate, an alpha-cyanoacrylate or a methacrylate; and linear, branched and cyclic alkyl ether residues of 1 to 20 carbons and 1 to 9 oxygens terminating in an acrylate, an alpha-chloroacrylate, an alpha-cyanoacrylate or a methacrylate.

15. A polymerizable oligomer according to claim 1, wherein FG is chosen from:
- linear, branched and cyclic alkyl residues of 1 to 20 carbons substituted with an epoxide;
- linear, branched and cyclic alkyl ether residues of 1 to 20 carbons and 1 to 9 oxygens substituted with an epoxide;
- arylalkyl residues of 1 to 20 carbons substituted with an epoxide; and
- arylalkyl ether residues of 1 to 20 carbons and 1 to 9 oxygens substituted with an epoxide.

16. A polymerizable oligomer according to claim 1, wherein FG is an epoxy-functional organosiloxane residue of 1 to 20 silicons and 1 to 20 carbons.

17. A process according to claim 6, wherein the ratio of alkoxy silane monomers of formula $(RO)_3SiFG$ to the alkoxy silane monomers of formula $R^3R^4R^8SiOR^{2a}$ ranges from 19:1 to 1:9, by weight.

18. A process according to claim 6, wherein the ratio of alkoxy silane monomers of formula $(RO)_3SiFG$ to the alkoxy silane monomers of formula $R^3R^4R^8SiOR^{2a}$ ranges from 3:1 to 1:1.

19. A process according to claim 6, wherein said one or more alkoxy silane monomers of formula $(RO)_3SiFG$ and one or more alkoxy silane monomers of formula $R^3R^4R^8SiOR^{2a}$ are reacted sequentially, and whereby a block oligomer is produced.

20. A process according to claim 6, wherein FG is chosen from linear, branched and cyclic alkyl residues of 1 to 20 carbons terminating in a 1-alkenyl ether; and linear, branched and cyclic alkyl ether residues of 1 to 20 carbons and 1 to 9 oxygens terminating in a 1-alkenyl ether.

21. A process according to claim 6, wherein FG is chosen from linear, branched and cyclic alkyl residues of 1 to 20 carbons terminating in an acrylate, an alpha-chloroacrylate, an alpha-cyanoacrylate or a methacrylate; and linear, branched and cyclic alkyl ether residues of 1 to 20 carbons and 1 to 9 oxygens terminating in an acrylate, an alpha-chloroacrylate, an alpha-cyanoacrylate or a methacrylate.

22. A process according to claim 6, wherein FG is chosen from:
- linear, branched and cyclic alkyl residues of 1 to 20 carbons substituted with an epoxide;
- linear, branched and cyclic alkyl ether residues of 1 to 20 carbons and 1 to 9 oxygens substituted with an epoxide;
- arylalkyl residues of 1 to 20 carbons substituted with an epoxide; and
- arylalkyl ether residues of 1 to 20 carbons and 1 to 9 oxygens substituted with an epoxide.

23. A process according to claim 6, wherein FG is an epoxy-functional organosiloxane residue of 1 to 20 silicons and 1 to 20 carbons.

* * * * *

UNITED STATES PATENT AND TRADEMARK OFFICE
CERTIFICATE OF CORRECTION

PATENT NO.    : 6,391,999 B1
DATED         : May 21, 2002
INVENTOR(S)   : Crivello It is certified that error appears in the above-identified patent and that said Letters Patent is hereby corrected as shown below:

<u>Column 16,</u>
Line 55, delete "i" at the end of the sentence and insert -- 1 --

Signed and Sealed this

Twenty-second Day of October, 2002

Attest:

Attesting Officer

JAMES E. ROGAN
*Director of the United States Patent and Trademark Office*